(12) United States Patent
Lord

(10) Patent No.: US 6,239,178 B1
(45) Date of Patent: May 29, 2001

(54) METHOD OF TREATING MAMMALS

(76) Inventor: George Dimelow Alexander Lord, 13 Station Street, Pymble, New South Wales 2073 (AU)

( * ) Notice: Subject to any disclaimer, the term of this patent is extended or adjusted under 35 U.S.C. 154(b) by 0 days.

(21) Appl. No.: 09/148,443

(22) Filed: Sep. 4, 1998

Related U.S. Application Data

(63) Continuation-in-part of application No. 08/859,818, filed on May 19, 1997, now abandoned.

(30) Foreign Application Priority Data

May 22, 1996 (AU) .................................................. PO0019
May 17, 1996 (AU) .................................................. PN9911

(51) Int. Cl.$^7$ ................................................ A61K 31/195
(52) U.S. Cl. ........................................................... 514/565
(58) Field of Search ............................................. 514/461

(56) References Cited

U.S. PATENT DOCUMENTS 5,204,344 * 4/1993 Prasit et al. ....................... 514/227.8

OTHER PUBLICATIONS

Chemical Abstracts 124: 52674w Costa, et al. (1996).
Chemical Abstracts 125: 272636w Gallai, et al. (1996).

* cited by examiner

*Primary Examiner*—Theodore J. Criares
(74) *Attorney, Agent, or Firm*—Ladas & Parry

(57) ABSTRACT

Symptoms of a headache can be reduced by reducing the concentration of arginine in the blood. This can be accomplished by administering an inhibitor of arginosuccinase that leads to an increase in nitric oxide levels. The inhibitor of arginosuccinase is a N3 or N2 and N3 substituted arginine. Mixtures of these inhibitors can be used.

2 Claims, 1 Drawing Sheet

METHOD OF TREATING MAMMALS

This application is a Continuation-in-Part of U.S. application Ser. No. 08/859,818, filed May 19, 1997, now abandoned.

TECHNICAL FIELD

This invention relates to a method of treating the symptoms of headache, migraine headache or recurring vascular disorders in a mammal, which conditions are indicated by low blood urea levels.

BACKGROUND ART

In humans, vascular disorders include headaches including wine headaches, migraine headaches and associated conditions. Typically migraines are a headache which can be characterised by a prodromal aura, unilateral onset, photophobia, severe pain, and autonomic disturbances during the acute phase, which may last for hours or days.

According to recent International Headache Society definitions, migraine can be divided into two broad clinical groups; migraine with typical aura and migraine without typical aura. The commonest clinical group being migraine without aura. Most patients with this form of migraine are women and many experience menstrual attacks. Migraine sufferers are acutely aware of their unpredictable unreliability and frequently avoid making social arrangements that they are scared they may be unable to fulfil, and on numerous occasions, rather than to be seen to let their colleagues down, many migraine sufferers prefer to tough it out and turn up at work, but often do not perform very competently.

Generally, the tendency to have migraine attacks is inherited and sufferers vary in the frequency of their attacks. Many have only one or two attacks a year and these usually result in a temporary social or work hiccup. Perhaps 10–15% of women experience one or more attacks per month and because of their unpredictability and the resulting unreliability, or reduction in competence of the sufferer, this group of patients experience substantial disruption to their activities.

There are two main forms or treatments used to counter the attacks. One is to take regular medication, trying to prevent the occurrence of the more severe unpleasant type of attack. The other is trying to treat such attacks as they occur, using either simple pain killers or specific anti-migraine treatments which are directed at the actual migraine process, attempting to stop individual attacks as soon as possible after onset.

OBJECTS OF THE INVENTION

It is a first object of the present invention to reduce the symptoms of headache including wine and migraine headache in humans.

It is a further object of the invention to provide a method of determining the cause of migraine in humans.

DISCLOSURE OF THE INVENTION

The present inventor has surprisingly found that many more than the expected number of human migraine sufferers have a low level of blood urea and therefore this blood condition is a marker for prospective migraine sufferers. Furthermore, migraine headaches are surprisingly thought to be a cause of erratic form in racehorses and greyhounds. Wine is also known to trigger biochemical reactions within the human body and it is thought that these reactions can be to some extent reversed, thereby at least reducing the symptoms.

According to a first aspect of this invention there is provided a method of reducing the symptoms of headache including wine and migraine headache in mammals said method comprising the step of reducing the concentration of arginine and as a consequence nitric oxide in the blood of the mammal and its arteries.

The method involves administering to a mammal a substance selected from the group consisting of:

(a) a substance which acts on the urea cycle to interfere with by reducing or preventing the production of arginine;

(b) an inhibitor of an enzyme which leads to an increase in nitric oxide levels;

(c) a substance which acts to remove ammonia from a mammal's body;

(d) a substance which reduces ammonia absorption by the mammal's body;

(e) an activator of arginase or inhibitor of arginine;

mixtures thereof and of other kinds of similar substances.

The concentration of arginine is usually reduced by activators of arginase or inhibitors of arginine. Typically any substance which acts on the urea cycle to interfere with by reducing or preventing the production of arginine, or acts to remove ammonia from a mammal's body, or reduces ammonia absorption by the mammal's body, or acts on the levels of nitric oxide in a mammal's body, mixtures thereof or of other kinds of similar substances may be used to reduce the concentration of arginine and nitric oxide. Other methods of reducing arginine and nitric oxide blood concentrations include blood transfusions so as to give blood, plasma or the like, and haemodialysis. The concentration of arginine and nitric oxide is usually reduced to a substantially normal level/concentration or within a substantially normal range/concentration in the blood of the mammal. A normal level/concentration of blood urea is normally indicative of a normal level/concentration of arginine and nitric oxide in the blood.

Examples of arginase activators and examples of inhibitors of arginine are hormones such as glucocorticoid and testosterone, possibly including adjusting physical stress levels experienced by the mammal.

Examples of substances which act on the urea cycle include inhibitors of the urea cycle such as excess levels of arginine: inhibitors of enzymes which lead to increased levels of nitric oxide such as inhibitors of arginosuccinase, arginosuccinic acid synthetase, carbamylphosphate synthetase, N acetylglutamate synthetase, arterial nitric oxide synthase; inhibitors of omithine transcarbamylase; gene replacement therapy for the defective gene which encodes for arginase, arginosuccinase, arginosuccinic acid synthetase, carbamylphosphate synthetase, N acetylglutamate synthetase, arterial nitric oxide synthase, ornithine transcarbamylase; substances which reduce the overall protein load, in particular reducing the amount of dietary arginine, aspartic acid and glutamic acid; substances which decrease the susceptibility of arginase to inhibition by extraneous substances including proline and branched chain amino acids or by changes in oestrogen and glucocorticoid levels or changes in the levels of the hormones involved in the menstrual cycle.

Examples of substances which act to remove ammonia from a mammal's body include antibiotics which reduce the production of gastrointestinal ammonia such as neomycin, or compounds such as sodium benzoate and phenyl acetate.

Examples of substances which reduce ammonia absorption by the mammal's body include charcoal and lactulose.

Examples of substances which act on the levels of nitric oxide in a mammal's body include inhibitors of nitric oxide production such as immunosuppresive agents like corticosteroids, azathioprine, antihymocyte globulin or cyclosporin.

This invention particularly relates to reducing the symptoms of headache including migraine and wine headaches in mammals by administering to the mammal an inhibitor of arginosuccinase.

The arginosuccinase inhibitors used for this treatment are typically N3 or N2 and N3 substituted arginines which include the following:

N3-(1-carboxy-2-methoxycarbonyl-ethyl)-L-arginine
N3-(1-carboxy-2-propoxycarbonyl-ethyl)-L-arginine;
N3-(1-carboxy-2-isobutoxycarbonylethyl)-L-arginine;
N3-(1-carboxy-3-N-ethylpropanamide)-L-arginine:
N3-(1,2-dimethoxycarbonylethyl)-L-arginine;
N3-(2-carboxy-1-methoxycarbonyl-ethyl)-L-arginine;
N3-(2-carboxy-1-propoxycarbonyl-ethyl)-L-arginine;
N3-(2-carboxy-2-isobutxycarbonylethyl)-L-arginine;
N3-(2-carboxy-1-N-ethylmethamidethyl)-L-arginine;
N3-(1-carboxy-2-nitroethyl)-L-arginine;
N2-methyl-N3-(L-1,2-dicarboxy-ethyl)-L-arginine;
N2-dimethyl-N3-(1,2-dicarboxy-ethyl)-L-arginine:
N2-propyl-N3-(1,2-dicarboxy-ethyl)-L-arginine;
N2-isobutyl-N3-(1,2-dicarboxy-ethyl)-L-arginine, and
N2-ethylamino-N3-(1,2-dicarboxy-ethyl)-L-arginine.

An investigation into the cause of migraine headaches indicates the arginase enzyme as a likely site of a defective enzyme in migraine, the mechanism being the unfettered production of arginine, thereby driving the production of the dilating and pain producing chemical nitric oxide.

While several studies have shown infusions of arginine have not produced migraine in either controlled subjects or migraineurs (see Costa, A. et al., 52874W, *Chemical Abstracts* Vol 124, No 5, 1996, p 52680 and Gallal, V. et al., 272636W, *Chemical Abstracts* Vol 125, No 21, 1996, 940), these studies do not exclude the possibility that arginine produced locally in the migraine vessel would not have this effect.

It appears that the critical point may well be how much arginine is present in the wall of the artery where the nitric oxide is being produced and as migraine attacks only occur intermittently, it would be common for the circumstances at the level of the migraine artery to be unsuitable for migraine production, irrespective of the blood level of arginine.

There are at least two isoforms of the arginase enzyme, the first being arginase type one, the hepatic form and the second, the arginase type 2, being found in various other organs, tissues and in particular in the arteries which are the site of the migraine vascular pain.

The arginase type 1 enzyme has not been found to be defective in migraine sufferers and it is thought that the likely candidate is an arginase enzyme which may be present in other tissues and in particular in the arteries which are the site of the migraine vascular pain.

The arginase type 2 enzyme is influenced by hormones including oestrogen and glucocorticoids, which is consistent with a role for such a hormonally sensitive enzyme in migraine.

A typical way to prevent the production of a build up in blood vessel arginine is to use an inhibitor to one of the more proximal enzymes in the urea cycle, the most likely candidate being arginosuccinase (arginosuccinate lyase).

Arginosuccinase deficiency exists naturally and when detected in adults seems to be without major toxicity. Thus administering a therapeutically effective amount of an arginosuccinase inhibitor can protect the patient from the development of high levels of arterial arginine and the unfettered production of nitric oxide which results in migraine headache.

Adult forms of arginoauccinase deficiency result in arginosuccinaciduria with an ammonium group being passed out in the urine thereby avoiding a build up of ammonia in the system and possible hepatic coma.

The headache in migraine and in particular in common migraine is episodic and intermittent and if one were to use an enzyme inhibitor to try and protect the artery from the defective pathway, the patient would only need this protection occasionally, the aim of the inhibition of the enzyme being to restore the nitric oxide production to normal levels of activity rather than to abolish it completely. This involves reducing the production of arterial arginine to a normal level rather than abolishing it altogether. This relatively "gentle" treatment rather than absolute abolition of activity is safe in that it does not produce gross biochemical distortions in relation to the urea cycle.

According to a further aspect of this invention there is provided a method of determining the course of treatment of a headache including wine and migraine headache in a mammal, said method comprising the steps of taking a blood sample and ascertaining the level of blood urea in the blood sample.

If the level of blood urea is low, and there are no underlying causes thereof, the abovementioned step of reducing the concentration of arginine and as a consequence nitric oxide in the blood is then taken.

Typically the normal level of blood urea in a normal human adult ranges from 3.6–9.3 mg/100 mL. Typically low levels of urea range from 1 to 5 mg/100 mL, usually a blood urea level below approximately 5 mg/100 mL is considered as low.

The means of determining the level of blood urea are well known. These involve removing a sample of blood and measuring the amount of nitrogenous substance present in the blood as urea, also known as BUN. BUN is a rough indicator of kidney function. An elevated BUN is a general indicator of kidney failure, shock, GI bleeding, diabetes mellitus and some tumours. A decreased BUN is a general indicator of liver disease, malnutrition and normal pregnancy.

Examples of mammals include humans, horses, dogs, including greyhounds, cats, camels and other like mammals.

The substance may be administered orally, parenterally, intramuscularly, or intravenously. The substance may be administered hourly, daily, weekly, monthly, or annually. Preferably the substance is administered orally or by injection.

BRIEF DESCRIPTION OF THE DRAWING

A preferred embodiment of the invention is now described with reference to FIG. 1 which is a schematic representation of some of the interrelationships of arginine and nitric oxide production.

BEST MODE FOR CARRYING OUT THE INVENTION

Figure 1:
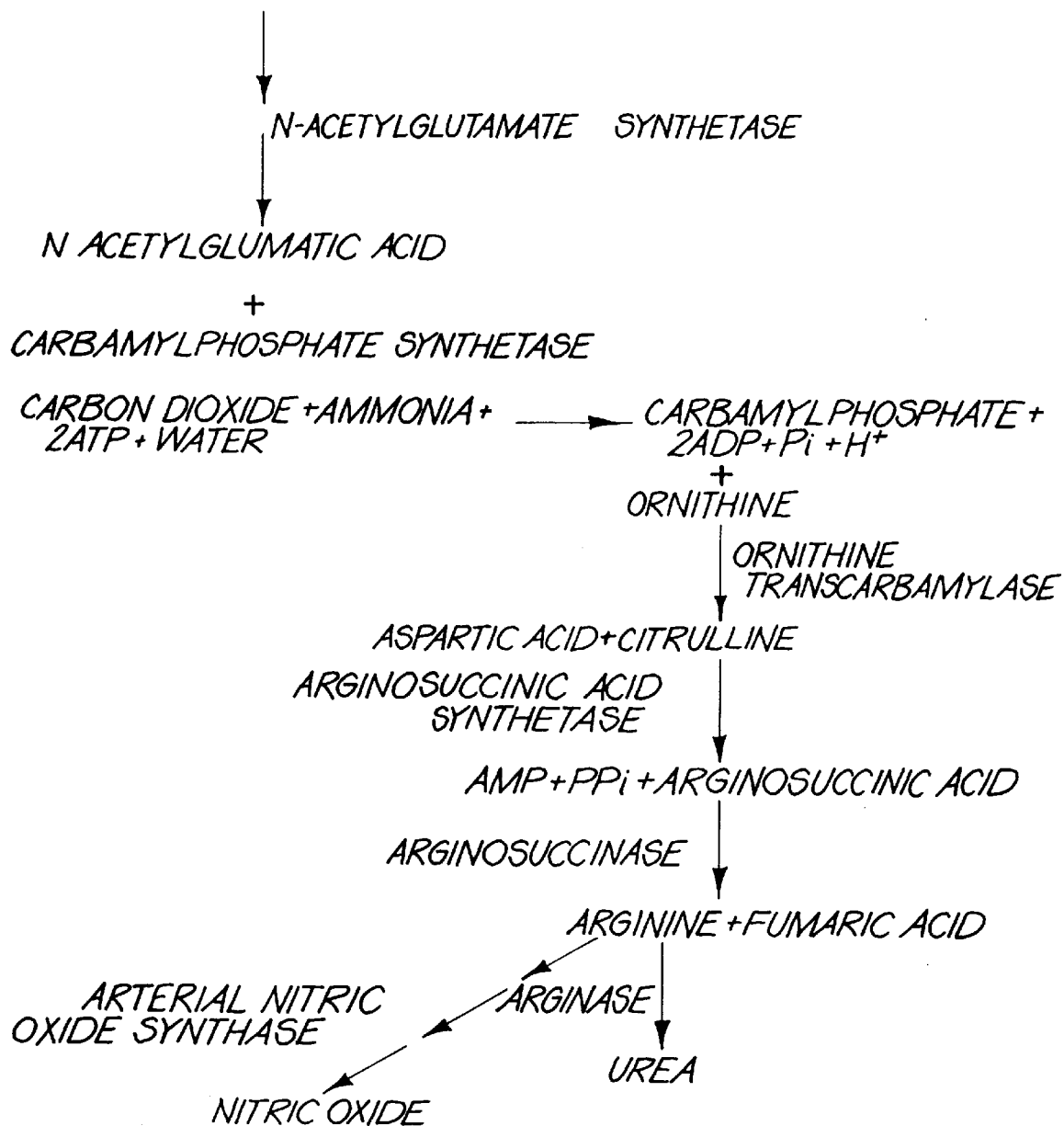

Typically to determine the course of treatment of a migraine in a human, a sample of blood is collected and the amount of blood urea is determined. If the blood urea level is in the range of 1 to 5 mg/100 mL, especially below about 5 mg/100 mL, tests are conducted to determine whether there is an underlying cause for the low level of blood urea, such as liver disease, malnutrition or pregnancy. If there is no underlying cause for the low level of blood urea, then the patient can be monitored and low levels of blood urea used to confirm the onset of a migraine due to high blood concentrations of nitric oxide.

Typically to reduce the symptoms of headache including migraine headache in mammals, the concentration of arginine and as a consequence nitric oxide in the blood of the mammal is reduced.

Usually the concentration of nitric oxide is increased due to an increase in the amount of arginine in a mammal's body. The increase in arginine can particularly be attributed to deficiencies in the activity or level of arginase resulting in a low level of blood urea and/or to increases in the activity or level of arginosuccinase, arginosuccinic acid synthetase, carbamylphosphate synthetase, N acetylglutamate synthetase, arterial nitric oxide synthase or omithine transcarbamylase or mixtures thereof. Alternatively, the increased concentration of nitric oxide is due to a defective gene encoding arginase which results in low levels of blood urea or a defective gene encoding arginosuccinase, arginosuccinic acid synthetase, carbamylphosphate synthetase, N acetylglutamate synthetase, arterial nitric oxide synthase, or ornithine transcarbamylase or mixtures thereof.

A typical means of reducing the concentration of arginine and nitric oxide is administering to the patient an arginosuccinic acid inhibitor to restore the production of nitric oxide and to reduce the production of arterial arginine.

Typically the arginosuccinase inhibitors used are N3 or N2 and N3 substituted arginines including the following:

N3-(1-carboxy-2-methoxycarbonyl-ethyl)-L-arginine;
N3-(1-carboxy-2-propoxycarbonyl-ethyl)-L-arginine;
N3-(1-carboxy-2-isobutoxycarbonyl-ethyl)-L-arginine;
N3-(1-carboxy-3-N-ethylpropanamide)-L-arginine:
N3-(1,2-dimethoxycarbonyl-ethyl)-L-arginine;
N3-(2-carboxy-1-methoxycarbonyl-ethyl)-L-arginine;
N3-(2-carboxy-1-propoxycarbonyl-ethyl)-L-arginine;
N3-(2-carboxy-2-isobutoxycarbonyl-ethyl)-L-arginine;
N3-(2-carboxy-1-N-ethylmethamide-ethyl)-L-arginine;
N3-(1-carboxy-2-nitroethyl)-L-arginine;
N2-methyl-N3-(L-1,2-dicarboxy-ethyl)-L-arginine:
N2-dimethyl-N3-(1,2-dicarboxy-ethyl)-L-arginine;
N2-propyl-N3-(1,2-dicarboxy-ethyl)-L-arginine;
N2-isobutyl-N3-(1,2-dicarboxy-ethyl)-L-arginine, and
N2-ethylamino-N3-(1,2-dicarboxy-ethyl)-L-arginine.

The administered dose of the arginosuccinase inhibitor and the duration of treatment with the inhibitor can vary and will depend on several factors such as the condition, age and size of the patient as well as the severity and extent of the condition, and related factors that will be decided by the attending physician.

Compositions of the arginosuccinase inhibitor for administration in the method of the invention may be prepared by means known in the art for the preparation of compositions (such as in the art of pharmaceutical compositions) including blending, grinding, homogenising, suspending, dissolving, emulsifying, dispersing and where appropriate, mixing of the herb together with selected excipients, diluents, carriers and adjuvants.

For oral administration, the pharmaceutical composition may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoata, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl disteaae.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropylmethyl-cellulose, polyvinylpyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further include one or more emulsifying agents. Suitable emulsifying agents include dispersing agents as exemplified above or natural gums such as gum acacia or gum tragacanth.

Compositions comprising an arginosuccinase active ingredient may also be administered parenterally, intramuscularly, or intravenously. The substance may be administered hourly, daily, weekly, monthly, or annually. Preferably the substance is administered orally or by injection.

Another means of reducing the arginine and nitric oxide is by administering blood or diluted plasma transfusion or haemodialysis. Another preferred means is by gene therapy to replace or repair the defective gene which encodes arginase. Another preferred means is by administering an effective amount of a suitable hormone.

By controlling the concentration of arginine and therefore nitric oxide as described particularly by way of administering an arginosuccinase inhibitor as previously described, it is possible to treat or prevent migraine.

EXAMPLE

When studying a sample of over 50 women with common migraine, more than half demonstrated an unexpectedly low blood urea level not attributable to reduced dietary protein intake, vomiting or pregnancy.

A major proportion of these migraine sufferers have a low level of blood urea when compared to controls, their only other abnormality being that they currently have a migraine attack. In the above sample approximately 25% have a blood urea concentration of less than 3.6 mg/100 mL, a further approximately 25% have a blood urea concentration of less than 4.2 mg/100 mL and overall approximately two thirds of the sample have a blood urea concentration of less than 5 mg/100 mL.

The combination of the low level of blood urea and the occurrence of migraine is believed to be due to reduced urea production caused by defective action of arginase leading to an increase in the availability of arginine for conversion to nitric oxide peripherally producing headache. An underlying cause of this defective enzyme activity is believed to be an inherited defective gene.

The sample of patients with low blood urea levels were randomly selected migraine patients and from families, some with X-linked inheritance and others with autosomal dominant inheritance with more than one family member being affected. This has led to the discovery that the majority of migraine attacks are due to a specific inherited defect in arginase function. It is this discovery which results in the possibility of taking measures to prevent migraine attacks.

The foregoing describes only one example of the present invention and modifications, obvious to those skilled in the art, can be made thereto without departing from the scope of the present invention.

For many years it has been known that wine can trigger headaches including s migraine headaches. Extreme variability between individuals is exhibited. Because the ingestion or injection of histamine is known and causes headaches, it had previously been thought that the "culprit" in wine was a histamine. However, in the light of the above the present invention indicates that the "culprit" in wine which causes headaches is a substance which increases the blood concentration of nitric oxide by way of increased concentration of arginine. Therefore to counteract such wine headaches a suitable course of treatment is to reduce the blood concentration of nitric oxide by any of the measures referred to herein and especially to reduce the presence of arginase inhibitors.

It is thought the present invention may be applicable to racehorses and greyhounds in particular since these racing mammals sometimes have erratic form which is thought to be due to migraine headaches.

What is claimed is:

1. A method for reducing symptoms of a headache in a mammal, which method comprises the step of reducing the concentration of arginine in the blood of the mammal and its arteries by administering to the mammal an inhibitor of an enzyme which leads to an increase in nitric oxide levels, wherein the enzyme is arginosuccinase and the inhibitor of arginosuccinase is a N3 or N2 and N3 substituted arginine, or a mixture thereof, wherein the N3 or N2 and N3 substituted arginine is selected from the group consisting of:

N3-(1-carboxy-2-methoxycarbonyl-ethyl)-L-arginine;
N3-(1-carboxy-2-propoxycarbonyl-ethyl)-L-arginine;
N3-(1-carboxy-2-isobutoxycarbonyl-ethyl)-L-arginine;
N3-(1-carboxy-3-N-ethylpropanamide)-L-arginine;
N3-(1,2-dimethoxycarbonyl-ethyl)-L-arginine;
N3-(2-carboxy-1-methoxycarbonyl-ethyl)-L-arginine;
N3-(2-carboxy-1-propoxycarbonyl-ethyl)-L-arginine;
N3-(2-carboxy-2-isobutoxycarbonyl-ethyl)-L-arginine;
N3-(2-carboxy-1-N-ethylmethamide-ethyl)-L-arginine
N3-(1-carboxy-2-nitroethyl)-L-arginine;
N2-methyl-N3-(L-1,2-dicarboxy-ethyl)-L-arginine;
N2-dimethyl-N3-(1,2-dicarboxy-ethyl)-L-arginine;
N2-propyl-N3-(1,2-dicarboxy-ethyl)-L-arginine;
N2-isobutyl-N3-1,2-dicarboxy-ethyl)-L-arginine; and
N2-ethylamino-N3-(1,2-dicarboxy-ethyl)-L-arginine.

2. A method as defined in claim 1 wherein the mammal is a human.

* * * * *